United States Patent [19]
Lane et al.

[11] Patent Number: 5,824,821
[45] Date of Patent: Oct. 20, 1998

[54] PROCESS FOR THE PREPARATION OF IODINATED CONTRAST AGENTS AND INTERMEDIATES THEREFOR

[75] Inventors: David Redick Lane, Davis, Calif.; Janis Vasilevskis, Berwyn, Pa.

[73] Assignee: Nycomed Imaging AS, Norway

[21] Appl. No.: 796,212

[22] Filed: Feb. 7, 1997

[51] Int. Cl.$^6$ .................. A61K 49/04; C07C 209/68; C07C 231/12

[52] U.S. Cl. .................. 564/153; 424/9.453; 424/9.454; 549/521; 549/523; 564/134; 564/156; 564/159; 564/183; 564/443; 564/487

[58] Field of Search .................. 549/521, 523; 564/134, 153, 156, 159, 183, 443, 487; 424/9.453, 9.454

[56] References Cited

U.S. PATENT DOCUMENTS

| | | | |
|---|---|---|---|
| 4,250,113 | 2/1981 | Nordal et al. | 564/153 |
| 4,358,615 | 11/1982 | Kleemann et al. | 564/475 |
| 5,191,119 | 3/1993 | Sovak et al. | 564/153 |

FOREIGN PATENT DOCUMENTS

| | | | |
|---|---|---|---|
| 0042376 | 3/1985 | Japan | 549/552 |

OTHER PUBLICATIONS

Bernadou et al., "Redox Tautomerism" in High Valent Metal–oxo–aquo Complexes. Origin of the Oxygen Atom in Epoxidation Reactions Catalyzed by Water–Soluble Metalloporphyrins, J. Am. Chem. Soc. 116:9375–9376, 1994.

Haavaldsen et al., "X–Ray Contrast Agents: 1. Synthesis of Some Derivatives of 5–amino–2,4,6–triiodoisophthalamide", Acta Pharm. Suec. 20:219–232, 1983.

Palucki et al., Highly Enantioselective, Low–Temperature Epoxidation of Styrene, J. Am. Chem. Soc. 116:9333–9334, 1994.

Venturello et al., "Quaternary Ammonium Tetrakis (diperoxotungsto)phosphates(3–) as a New Class of Catalysts for Efficient Alkene Epoxidation with Hydrogen Peroxide", J. Org. Chem. 53:1553–1557, 1988.

Venturello et al., "A Convenient Catalytic Method for the Dihydroxylation of Alkenes by Hydrogen Peroxide", Synthesis Communications pp. 295–297, 1989.

*Primary Examiner*—Richard L. Raymond
*Attorney, Agent, or Firm*—Fish & Richardson P.C.

[57] ABSTRACT

The invention provides a process for the production of a 2,3-dihydroxypropylamino compound, said process comprising the reaction steps of:

(i) obtaining an allylamino compound;

(ii) epoxidizing said allylamino compound to yield an epoxypropylamino compound; and (iii) hydrolysing said epoxypropylamino compound to yield a 2,3-dihydroxypropylamino compound.

This process may be used to produce simple 2,3-dihydroxypropylamino compounds such as APD or complex ones such as BAPD (an intermediate in the production of iohexol).

9 Claims, No Drawings

PROCESS FOR THE PREPARATION OF IODINATED CONTRAST AGENTS AND INTERMEDIATES THEREFOR

FIELD OF THE INVENTION

This invention relates to a process for the preparation of iodinated X-ray contrast agents, to key intermediates in the preparation of such contrast agents and to processes for the preparation of such intermediates.

BACKGROUND OF THE INVENTION

Iodinated organic compounds, in particular triiodophenyl monomer and dimer compounds, have long established and widespread commercial use as X-ray contrast agents. Initially, the commercially available compounds were ionic compounds (eg. metrizoate, iodipamide, iodamide, iobenzamate, iocarmate, iocetamate, iodoxamate, ioglicate, ioglycamate, iopanoate, iophendylate, iopronate, ioserate, iothalamate, iotroxate, ioxaglate and ioxitalamate) but more recently the dominant commercial iodinated X-ray contrast agents have been the non-ionic compounds (such as iohexol, iopamidol, iomeprol, iopentol, iopromide, iosimide, iotasul, iotrolan, ioversol, metrizamide and iodixanol) which may be administered parenterally at higher concentrations and with reduced adverse effects.

The non-ionic compounds derive their necessary water-solubility from the presence in their molecular structures of non-ionic solubilizing groups such as hydroxyalkyl groups. Thus by way of example, iohexol, iopentol and iodixanol have the monomeric and dimeric triiodophenyl structures incorporating solubilizing hydroxyalkyl groups that are shown below:

IOPENTOL

IOHEXOL

IODIXANOL

The preparation of such compounds involves the introduction of a 2,3-dihydroxypropylamino group at ring attached carbonyls. As described by Haavaldsen et al. in Acta Pharm Suec 20: 219–232 (1983), this is achieved by reacting 3-amino-1,2-propanediol (APD) with a ring attached carboxyl group. A similar reaction is discussed in U.S. Pat. No. 4,250,113 (Nyegaard & Co.).

APD has thus been a critical reagent in the synthesis of the commercial 2,3-dihydroxypropylaminocarbonyltriiodophenyl X-ray contrast agents.

There has however been a major problem in producing APD with sufficiently high purity (eg. $\geq 99.9\%$). One synthetic approach to APD production involves the reaction of glycidol (1-hydroxy-2,3-epoxypropane) with ammonia. Not only is this reaction potentially explosive but the reaction product is a mixture of APD and 2-amino-1,3-propanediol. Purification of the reaction product requires a very difficult distillation since the boiling point difference between the two aminodiols is very small.

An alternative approach has been to epoxidate allyl chloride, hydrolyse to produce 1-chloro-2,3-propanediol, and displace the chlorines with ammonia to yield APD. However, the basic conditions used can lead to reformation of the epoxide with the reaction with ammonia then yielding some of the undesired 2-amino product. Again therefore the difficult distillation is required to yield high purity APD.

A further approach has been to avoid the use of epoxides altogether and generate the diol group directly from an allyl group by oxidation with osmium tetroxide (see U.S. Pat. No. 5,191,119 (Cook Imaging)). This approach however involves use not only of osmium tetroxide but, as an intermediate, of isophthaloyl chloride. Synthesis of isophthaloyl chloride is an environmentally unfriendly reaction and the use of the highly poisonous osmium tetroxide in one of the final preparative steps for a product which is to be injected into patients is unacceptable.

SUMMARY OF THE INVENTION

We have now found that 2,3-dihydroxypropylamino compounds (such as APD) can be produced without 2-amino contamination by epoxidation of an allylamine followed by hydrolysis. Moreover the epoxidation and hydrolysis reactions may be performed on an allylaminocarbonylphenyl compound thus rendering the use of APD in the preparation of contrast agents such as iohexol quite unnecessary.

Viewed from one aspect therefore the invention provides a process for the production of a 2,3-dihydroxypropylamino compound, said process comprising the reaction steps of:

(i) obtaining an allylamino compound;
(ii) epoxidizing said allylamino compound to yield an epoxypropylamino compound; and
(iii) hydrolysing said epoxypropylamino compound to yield a 2,3-dihydroxypropylamino compound.

At its simplest, the process of the invention may have allylamine as the allylamino starting compound for step (i) and APD as the 2,3-dihydroxypropylamino product of the step (iii).

DETAILED DESCRIPTION OF THE INVENTION

To enhance reaction rates or yields in the process of the reaction it may be desirable to select as the allylamino starting compound an N-substituted or N,N-disubstituted compound, the substituents being selected to reduce the electron donor power of the nitrogen. Preferably, the allylamino starting compound will have one or two N-acyl substituents. Such substituents may be small (eg. groups containing up to six carbons) or large (eg. groups containing up to 50 carbons) and may be removed in the hydrolysis step (iii) or may be allowed to remain in the 2,3-dihydroxypropylamino product of step (iii).

Examples of suitable acyl groups include alkylcarbonyl, arylcarbonyl, aralkylcarbonyl, alkarylcarbonyl, and arylalkylarylcarbonyl groups in which any alkyl or alkylene moieties may be straight chain or branched and in the alkyl or alkylene moieties any backbone carbons not adjacent to the acylcarbonyl may be replaced by nitrogens or oxygen atoms or substituted by oxo, hydroxy or other groups and in which the aryl groups themselves are optionally substituted, eg. by nitro, halo (eg. iodo), alkylaminocarbonyl, alkenylaminocarbonyl, amino, alkylamino, and N-alkyl-acylamino groups. Aryl groups will preferably be carbocyclic groups with 6 to 10 ring atoms, and alkyl, alkylene, alkenyl and acylamino groups will preferably contain up to 6 carbon atoms, eg. methyl, ethyl, propyl, allyl, vinyl, acetamido, etc.

Such acyl groups thus include structures which are present in the X-ray contrast agents such as iohexol or in intermediates for such agents (eg. the pre-iodination compounds).

Preferred starting materials for step (i) of the process of the invention include N,N-bisacyl-allylamines (eg. N,N-bisacetyl-allylamine) and 1,3-bis(allylaminocarbonyl) benzenes (eg. 1,3-bis(allylaminocarbonyl)-5-nitro-benzene and 1,3-bis(allylaminocarbonyl)-2,4,6-triiodo-5-nitro-benzene. N,N-bis-acetyl-allylamine may be prepared for example by treatment of allylamine with acetic anhydride, while the 1,3-bis(allylaminocarbonyl)benzenes may be prepared for example by reacting alkylamine with an isophthalic acid diester, eg. the methyl diester.

Thus by way of example, reaction schemes 1 and 2 below illustrate the use of the process of the invention for the preparation of simple structures such as APD and more complex structures such as 5-nitro-isophthalic acid bis (amide-1-propane-2,3-diol) (BAPD) a key intermediate in the production of iohexol. Indeed BAPD is the intermediate conventionally produced by reaction of APD with 5-nitro-isophthalic acid or its dimethyl ester.

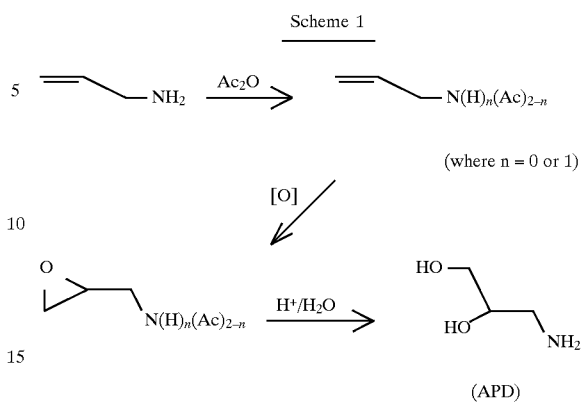

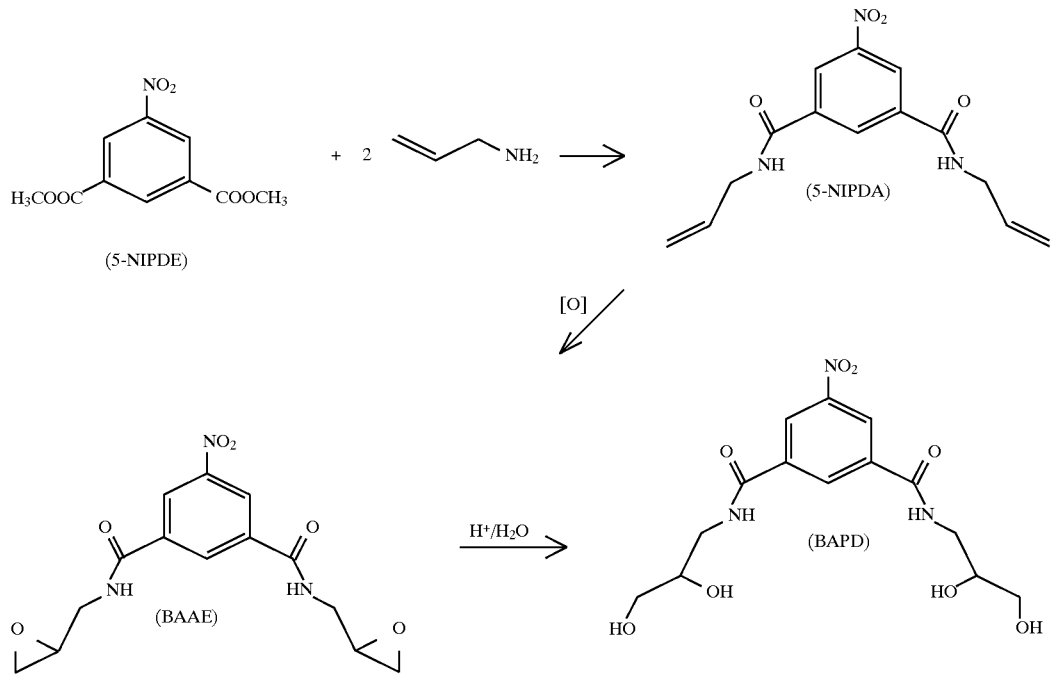

The oxidation of the allyl group in the process of the invention may be carried out with a range of oxidant and/or catalyst systems. Suitable oxidants include air, oxygen, hydrogen peroxide, hypochlorite and organic peroxides such as metachloroperbenzoic acid. Oxidants such as air, oxygen and hydrogen peroxide can be used to generate in situ a more effective oxidant species—thus for example a mixture of hydrogen peroxide and acetic acid will generate the oxidant peracetic acid. For the catalyst, where this is used, a wide number of metals and their compounds (eg. oxides, complexes etc.) may be used. Examples of suitable catalyst metals include Ti, V, Mn, Fe, Co, Mo, Ru, Rh, W, Re and Os (although $OsO_4$ and $RuO_4$ should not be used). For examples of catalyst systems reference may be made to Venturello et al. J. Org. Chem. 53: 1553–1557 (1988), Venturello et al. Synthesis, Communications 295–297 (April 1989), Palocki JACS 116: 9333–9334 (1994) and Bernadou JACS 116: 9375–9376 (1994). The selection of a catalyst will depend to a large extent on whether the diolamino product is itself to be used as a contrast agent or is a late stage intermediate for a contrast agent. In these cases, use of highly toxic catalysts should be avoided.

The epoxypropylaminocarbonylphenyl compounds which may be produced using the process of the invention, eg. the compound BAAE, are themselves new and form a further aspect of the invention. Similarly the product 5-NIPDA is new and forms a further aspect of the invention.

Where the intended end product of the process of the invention is APD, since this is a small molecule which can readily be freed from starting material and catalyst contamination by distillation, a direct 2,3-dihydroxylation of the allylamino starting compound (eg. allylamine, N-acetyl-allylamine or N,N-bisacetyl-allylamine) may be effected using for example catalysts such as $OsO_4$ and $RuO_4$. Thus viewed from a further aspect the invention provides a process for the preparation of APD, said process comprising 2,3-bishydroxylating an optionally N-acylated or N,N-bisacylated allylamine and if required hydrolysing an N-acyl or N,N-bisacyl-2,3-dihydroxypropylamine reaction product.

In the process of the invention, the hydrolysis step, step (iii) may be effected using conventional hydrolysis techniques, eg. acid catalysis. The hydrolysis conditions may be selected to remove or leave any acyl substituent on the epoxypropylamino nitrogen.

For the production of 2,3-dihydroxypropylamino X-ray contrast agents, in particular non-ionic contrast agents containing a 1-(2,3-dihydroxypropylaminocarbonyl)-2,4,6-triiodo-phenyl structural component such as iohexol, iopentol and iodixanol, the process of the invention may include one or more of the following process steps:

(iv) iodinating a 2,3-dihydroxypropylaminoacarbonylphenyl compound;

(v) converting a phenyl group substituent in a 2,3-dihydroxypropylaminoacarbonylphenyl compound into a solubilizing group, eg. a hydroxylated and/or alkoxylated group, for example an alkylaminocarbonyl or alkylcarbonylamino group (optionally carrying an N-acyl substituent, eg. $CH_3CO$); and (vi) conjugating two 2,3-dihydroxypropylaminoacarbonylphenyl compounds to produce a dimeric compound.

Thus, as described by Haavaldsen (supra), non-ionic contrast agents may conveniently be produced following a process scheme such as the following:

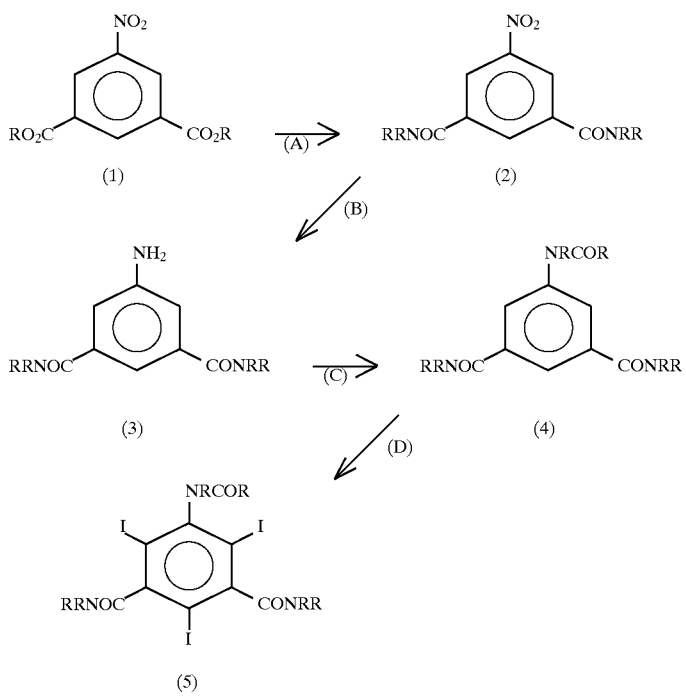

where the iodination of step (D) is omitted if iodination has been effected earlier, eg. prior to the production of the 5-nitro-isophthalic acid bis ester starting product (1), or if iodination has been effected before steps (A), (B) or (C). (Haavaldsen (supra) suggested iodination before step (C)). The R groups in the scheme set out above are not differentiated. The specific groups chosen would clearly depend upon the desired end product. Thus in the case of the use of the process of the invention to produce iohexol, step (A) will conveniently involve the reaction of 5-NIPDE with allylamine to produce 5-NIPDA, epoxidation to BAAE and hydrolysis to produce BAPD which is subsequently reduced, acetylated, N-hydroxyalkylated and iodinated.

The patents and other references mentioned herein are hereby incorporated by reference.

The invention will now be described further with reference to the following non-limiting Examples. The starting products, intermediates and end products were analysed by HPLC and $^{13}C$ NMR. The HPLC system used relied on absorption at 240 nm (where the benzene ring absorbs). The HPLC system was all glass Dionex; used a Supelcosil LC-18 DB column; used as eluant 72% methanol, 6.0 mM tetrabutylammonium bisulfate, 4.0 mM sodium hydroxide; had a flow rate of 1.0 mL/min and a sample volume of 25 μL; and used a UV detector at 240 nm. The HPLC retention times in minutes were as set out in Table 1 below:

TABLE 1

| | |
|---|---|
| 5-nitro-isophthalic acid bis(amide-1-propane-2,3-diol) (BAPD) I | 2.87 |
| N-(propane-2,3-diol)-benzamide | 2.87 |
| 5-nitro-isophthalic acid bis(amide-1-propane-2,3-diol) (BAPD) II | 2.98 |
| 5-nitro-isophthalic acid bis(allylamide epoxide) (BAAE) | 3.12 |
| N-allyl-benzamide epoxide | 3.30 |
| 5-nitro-isophthalic acid | 3.40 |
| 5-nitro-isophthalic acid 1-allylamide-3-allylamide epoxide | 3.48 |
| N-allyl-benzamide | 3.58 |
| 5-nitro-isophthalic acid bis(allylamine) (5-NIPDA) | 4.05 |
| m-chloro-perbenzoic acid | 4.50 |
| m-chloro-benzoic acid | 5.4–6.1 |
| 5-nitro-isophthalic acid dimethyl ester (5-NIPDE) | 6.25 |

It should be noted (a) that retention times slow down unless a freshly prepared eluant is used, and (b) BAPD gives two peaks.

Table 2 below lists the $^{13}$C peak assignments for the 5-nitro-isophthalic acid derivatives 5-NIPDA, BAAE and BAPD:

| | 5-NIPDA | BAAE | BAPD |
|---|---|---|---|
| E | 163.6 | 164.0 | 166.5 |
| D | 147.9 | 148 | 148 |
| A | 134.8 | 135.1 | 135.6 |
| B | 132.3 | 130.7 | 132.1 |
| C | 124.2 | 124 | 125 |
| F | 41.8 | 41.0 | 43.1 |
| G | 136.0 | 44.7 | 63.9 |
| H | 115.7 | 49.8 | 70.8 |

EXAMPLE 1

N-allyl-benzamide (NAB) was purchased from Monomer-Polymer Laboratories. It was determined to be 99.5% pure. Chromatography using chloroform and silica gel increased the purity of NAB to 99.9%. 1.05 g of the purified NAB was treated with a solution of 2.14 g of m-chloro-perbenzoic acid (MCPBA) in 15 mL of THF. After 64 hours at room temperature HPLC showed that no MCPBA remained. Conversion was 89.7% with 15.8% selectivity to (BAPD) and 78.7% selectivity to the 5-nitro-isophthalic acid bis(allylamide epoxide) (BAAE).

EXAMPLE 2 (Comparative)

23.9 g of 5-nitro-isophthalic acid dimethyl ester was added to 60 mL of boiling methanol followed by 21.84 g of 1-amino-propane-2,3-diol (APD). A white solid formed. Another 100 mL of methanol was added and the mixture was heated over the weekend. The white product was filtered from the hot solution, it was then washed with a small amount of methanol and was dried in a vacuum oven. The isolated yield of 5-nitro-isophthalic acid bis(amide-1-propane-2,3-diol) (BAPD) was 19.5 g. Identified by $^1$H and $^{13}$C NMR.

EXAMPLE 3

Fifty grams of 5-nitro-isophthalic acid dimethylester (5-NIPDE) was dissolved in 75 mL of methanol and 100 mL of allylamine. The solution was heated under nitrogen at reflux for approximately ten hours. TLC showed that the conversion was complete. About a liter of a one to one mixture of methanol/water was added. The solution was heated and became clear at 59° C. Some more water was added and the temperature was raised to 75° C. The solution was allowed to cool slowly to room temperature with stirring. The product was filtered off and dried at 50° C. in a vacuum oven. The product was dissolved in hot ethanol and cooled slowly to 4° C. Filtration followed by repeat drying yielded 47.82 g of product (79% yield). A second crop can be easily obtained from the remaining filtrates (Overall yield 94%). The material was identified by HPLC, NMR and MS as the 5-nitro-isophthalic acid bis(allylamide) (5-NIPDA).

EXAMPLE 4

1.27 g of 5-NIPDA were dissolved in 15 mL of THF. m-Chloroperbenzoic acid (MCPBA) was determined to have 57% of its peroxide activity left. 3.09 g of this material was added representing a 1.16 fold excess of peroxide over allyl substituents. The reaction was stirred at room temperature and HPLC showed an 80% conversion in about six hours. The reaction was left overnight. The conversion to the diepoxide (BAAE) was complete. Work-up included addition of methylene chloride and water containing sodium carbonate or bicarbonate. The organic fractions were combined. Removal of solvent yielded 0.80 g of a glass. HPLC showed the sample to have a purity of 73%. Mass spectroscopy showed a peak corresponding to the addition of two oxygens corresponding to the bis allyl epoxide (BAAE), further confirmed by $^{13}$C NMR (49.8, 44.7 ppm).

EXAMPLE 5

347 mg of BAAE were dissolved in 3 mL of THF. The solution was split into two portions. To one portion was added a catalytic amount of HCL while to the other was added a catalytic amount of NaOH. Both solutions showed hydrolysis to the bis diol (BAPD) as determined by HPLC and comparison to authentic material made by the prior art synthesis (Example 2).

EXAMPLE 6

1.0 g of 5-NIPDA was dissolved in 20 mL of glacial acetic acid. One mL of 30% hydrogen peroxide was added and the reaction mixture was heated to 88° C. After three hours HPLC showed a 9% conversion with an 80% selectivity to diol (BAPD). Water in the peroxide led to the epoxide hydrolysis and to an 8% hydrolysis of 5-NIPDA to 5-nitro-isophthalic acid. The epoxidation proceeds through the in situ generation of acetyl peroxide from hydrogen peroxide and acetic acid.

We claim:
1. A process for the production of a 2,3-dihydroxylpropylamino compound, said process comprising the reaction steps of:
   epoxidizing an N-acyl or N,N-bisacyl substituted allylamino compound to yield an N-acyl or N,N-bisacyl substituted epoxypropylamino compound;

hydrolysing said N-acyl or N,N-bisacyl substituted epoxypropylamino compound to yield an N-acyl or N,N-bisacyl substituted 2,3-dihydroxylpropylamino compound.

2. A process as claimed in claim 1 wherein said allylamino compound is of formula

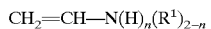

where n is zero or 1 and $R^1$ is an acyl group containing up to 50 carbons.

3. A process as claimed in claim 2 wherein $R^1$ is acetyl.

4. A process as claimed in claim 2 wherein n is 1 and $R^1$ is a benzoyl group.

5. A process as claimed in claim 4 wherein said allylamino compound is 5-nitro-isophthalic acid bis allylamide.

6. A process as claimed in claim 1 further comprising at least one of the following steps:

(iv) iodinating a 2,3-dihydroxypropylaminoacarbonylphenyl compound;

(v) converting a phenyl group substituent in a 2,3-dihydroxypropylaminoacarbonylphenyl compound into a solubilizing group; and (vi) conjugating two 2,3-dihydroxypropylaminoacarbonylphenyl compounds to produce a dimeric compound, whereby to produce an iodinated X-ray contrast agent.

7. A process as claimed in claim 6 wherein said allylamino compound is 5-nitro-isophthalic acid bis allylamide and steps (iv) and (v) are effected to yield iohexol.

8. A process as claimed in claim 1 wherein epoxidation in step (ii) is effected using an oxidant.

9. A process as claimed in claim 1 wherein epoxidation in step (ii) is effected using catalytic oxidation.

* * * * *